United States Patent [19]
Shen et al.

[11] Patent Number: 5,910,140
[45] Date of Patent: Jun. 8, 1999

[54] LASER MEDICAL DEVICE

[75] Inventors: Hong Yuan Shen; Rui Rong Zeng; Yu Ping Zhou; Gui Fang Yu; Cheng Hui Huang; Zheng Dong Zeng; Wen Xiong Lin; Rui Fen Wu, all of Fuzhou, China

[73] Assignee: Fujian Institute of Research on the Structure of Matter, Chinese Academy of Sciences, Fujian, China

[21] Appl. No.: 08/312,780

[22] Filed: Sep. 27, 1994

[30] Foreign Application Priority Data

Sep. 27, 1993 [CN] China .............................. 93 1 17719

[51] Int. Cl.$^6$ .................................. A61N 5/02; H03F 7/00
[52] U.S. Cl. ......................................................... 606/3
[58] Field of Search .................. 606/2, 10, 11, 606/13, 16, 17

[56] References Cited

U.S. PATENT DOCUMENTS

| | | | |
|---|---|---|---|
| 4,165,469 | 8/1979 | Ammann | 307/426 |
| 5,036,520 | 7/1991 | Bowman et al. | 372/41 |
| 5,150,704 | 9/1992 | Tatebayashi et al. | 606/10 |
| 5,181,214 | 1/1993 | Berger et al. | 372/34 |
| 5,312,396 | 5/1994 | Feld et al. | 606/10 |
| 5,336,217 | 8/1994 | Bugs et al. | 606/10 |

OTHER PUBLICATIONS

"YAlO$_3$ Doping TR$^{3+}$ Ions as Medium of Laser" by H.S. Bagdasarov et al, Letters of JETP, vol. 9, P501–502, Mar. 5, 1969.

M. J. Weber et al, Czochraski growth and properties of YAlO, laser crystals, Appl. Phys. Lett., vol. 15, p342(1969).

X. C. Bagdacarov et al, "YAlO$_3$ doping TR$^{3+}$ ions as active medium of laser", Pis'ma, ZH. Ehksp. Tear. Fiz., vol. 9, No. 9, p501(1969).

G. A. Mass et al, "High average power operation and nonlinear optical generation with the Nd:YAlO$_3$ laser", Appl. Phys. Lett., vol. 18, No. 2, p576(1971).

A. A. Kaminskii et al, "Anisotropy of spectroscopic characteristics in the biaxial YAlO$_3$–Nd$^{3+}$ laser crystals", Phys. Stat. Sol. (a)51, p509(1979).

H. Y. Shen, Thermal effects in orthorhombic YAP crystals, Acta Physica Sinica, vol. 30, No. 8, p1085(1981).

H. Y. Shen et al, "Influence of thermal effects on high power CW laser output of b–axis Nd:YAP", Chinese Physics, vol. 3, No. 1, p45(1983).

H. Y. Shen et al, "A high power 1079.5nm Nd:YAlO$_3$ CW laser", Chinese Journal of Lasers, vol. 19, No. 1, p19(1992).

(List continued on next page.)

*Primary Examiner*—Beverly M. Flanagan
*Assistant Examiner*—Sonya C Harris

[57] ABSTRACT

The laser medical device includes a Nd:YAlO$_3$ laser crystal; a pumping system which illuminates the laser crystal with light irradiated from a pumping light source and achieves population inversion of Nd$^{3+}$ ion in the laser crystal; and a resonant cavity for resonating light emitted from the Nd$^{3+}$ ion to output a laser light having a predetermined wavelength, wherein the wavelength of the laser light falls within the transparent range of quartz optical fibers. The laser medical device may also include a quartz optical fiber for transmitting the laser light; an optical fiber injector for focusing the laser light output by the resonant cavity on one end of the optical fiber; and an optical fiber pen which is coupled to another end of the optical fiber for aiming the laser light transmitted through the optical fiber at a desired location of a subject. These devices use Nd:YAlO$_3$ crystal as an active laser material and output laser light having a wavelength, such as 1341.4 nm and 1079.5 nm, within the transparent range of the quartz optical fiber. In such a band, Nd:YAlO$_3$ laser crystal has good performance characteristics for becoming a high power CW laser or a large energy pulsed laser. Therefore, Nd:YAlO$_3$ crystal can be used to develop laser medical devices having good clinical effects that are convenient for therapy such as for endoscopic operations.

13 Claims, 6 Drawing Sheets

OTHER PUBLICATIONS

H. Y. Shen et al, "Measurement of the stimulated emission cross section for $^4F_{3/2}$–$^4I_{13/2}$ transition of $Nd^{3+}$ ion in $YAlO_3$ crystal", IEEEJ Quantum Electron, vol. 25, No. 2, p144(1989).

Y. P. Zhou et al, "A method for calculating optomechanical coefficient of laser materials", Chinese Journal of Lasers, Special Issue on Laser Devices, vol. 17, p138(1990).

H. Y. Shen et al, "Laser action of $Nd:YAlO_3$ at 1300nm", Journal of Applied Physics, vol. 70, No. 6, p3373(1991).

H. Y. Shen et al, "Large Energy 1341.4nm $Nd:YAlO_3$ pulse laser", Opt. and Laser Technology, vol. 23, No. 6, p366(1991).

LASER MEDICAL DEVICE

BACKGROUND OF THE INVENTION

This invention is concerned with a medical laser device, especially with a medical device which outputs a laser light that can be transmitted through a general medical optical fiber, and which can output high laser power and can be conveniently used in clinical treatments.

A $CO_2$ gas laser medical machine is a commonly used type of laser medical device, whose 10.6 μm output laser power is almost absorbed by water and tissue of the human body, and whose laser light has a low penetrating ability through tissue. Therefore, it is widely used in gasification and incision of the surface focus of infection. But 10.6 μm $CO_2$ laser light cannot be transmitted through the general medical quartz fiber. Although a lot of funds have been invested to research a kind of infrared optical fibre which can transmit 10.6 μm $CO_2$ laser light, the progress is slow and the cost of fibre is much higher than that of the quartz optical fibre. Moreover, it is inconvenient to use a flexible joint arm to transmit light, and impossible to be used in endoscopic operations.

Additionally, 10.6 μm $CO_2$ light has a low penetrating ability through tissue, and it is hard to reach deeper micro vessels, so it is not so good to stanch bleeding. As is known to all, laser light at different wavelength has different effects on the organism. Therefore, it is necessary to develop other new wavelength and highly effective laser medical devices for clinical applications.

SUMMARY OF THE INVENTION

It is therefore an objective of the present invention to provide a laser medical device which outputs a laser light that can be transmitted through general medical optical fibre, and which can output high laser power and can be conveniently used in clinical treatments.

It is another objective of the present invention to provide a laser medical device which outputs a laser light that can be transmitted through general medical optical fibre, and which has a similar curative effect as that of a $CO_2$ laser medical machine.

It is yet another objective of the present invention to provide a laser medical device which outputs a laser light that can be transmitted through general medical optical fibre, and which can be used to solidify deep micro vessels and stanch bleeding.

It is a further objective of the present invention to provide a laser medical device which outputs a laser light that can be transmitted through general medical optical fibre, which can output partially polarized laser light and has special curative effects.

The laser medical device of this invention includes: an $Nd:YAlO_3$ laser crystal; a pumping system which illuminates said laser crystal with light irradiated from a pumping light source and achieves population inversion of $Nd^{3+}$ ion in said laser crystal; and a resonant cavity for resonating light emitted from said $Nd^{3+}$ ion to output a laser light having a predetermined wavelength, wherein the wavelength of said laser light falls within the transparent range of quartz optical fibres.

According to another aspect of this invention, the laser medical device which is adapted to internal or external body treatments further includes: a quartz optical fibre for transmitting said laser light; an optical fibre injector for focusing the laser light outputted by said resonant cavity on one end of said optical fibre; an optical fibre pen which is connected to another end of said optical fibre for aiming the laser light transmitted through said optical fibre at a desired location of a subject.

These devices use $Nd:YAlO_3$ crystal as their active laser material and output laser light having wavelengths within the transparent range of the quartz optical fibre. In such a band, $Nd:YAlO_3$ laser crystal has very good performance characteristics for becoming a high power CW laser or a high energy pulsed laser. Therefore $Nd:YAlO_3$ crystal can be used to manufacture laser medical devices which have good clinical effects. Moreover, these devices are allowed to utilize general optical fibre, so they are very convenient for operations and capable of being used in endoscopic operations.

BRIEF DESCRIPTION OF THE DRAWINGS

These and other features and effects of this invention will become clear through the following description of exemplary embodiments in detail with reference to the accompanying drawings, in which.

DETAILED DESCRIPTION OF THE PREFERRED EMBODIMENT

Figure 1:
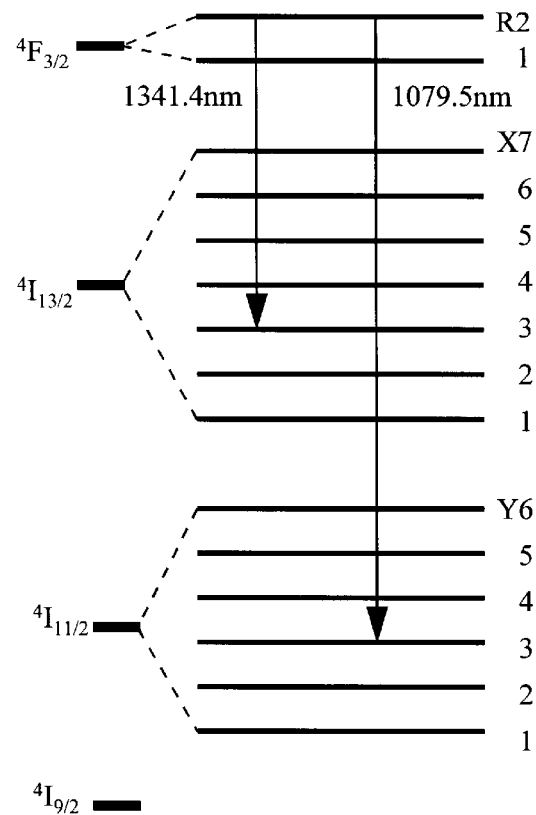
FIG. 1 shows the energy levels of $Nd^{3+}$ ion in $YAlO_3$ crystal.

FIG. 1 shows the energy levels of $Nd^{3+}$ ion in $YAlO_3$ crystal. The level of $^4F_{3/2}$ of $Nd^{3+}$ ion is a metastable level, and $^4I_{11/2}$ as well as $^4I_{13/2}$ is the level of terminal state of transition. When the light at corresponding wavelength (for example, the light irradiated from a Krypton lamp or Xenon lamp) illuminates the $Nd^{3+}$ doped $YAlO_3$ crystal, the $Nd^{3+}$ ions in the ground level are excited to transit to the excited states, then these $Nd^{3+}$ ions located at excited levels spontaneously transit to the metastable levels. Therefore the population of $Nd^{3+}$ ions of the metastable level is larger than that of the level of $^4I_{11/2}$ or $^4I_{13/2}$ with $Nd^{3+}$ ions being pumped by the exciting light, thus being able to form laser transitions and achieving laser light at some wavelengths. Under the action of $YAlO_3$ crystal field, the level of $^4F_{3/2}$ separates, as shown in FIG. 1, to levels $R_1$ and $R_2$, the level of $^4I_{13/2}$ to seven Stark sub-levels ($X_1$–$X_7$), while the level of $^4I_{11/2}$ to six Stark sub-levels ($Y_1$–$Y_6$). The transition from the metastable level of $^4F_{3/2}$ to the terminal state level of $^4I_{11/2}$ or $^4I_{13/2}$ generates about 1000 nm laser light, for example, the transition from level $R_1$ to level $Y_3$ generates 1079.5 nm and C-axis polarized laser light while the transition from level $R_2$ to level $X_3$ generates 1341.4 nm and C-axis polarized laser light. Both these wavelengths are among the transparent range of quartz optical fibre. Therefore a beam coming from the laser device using $Nd:YAlO_3$ as its laser active medium can be transmitted by general quartz medical optical fibre.

In the 1970's, the inventors of this invention found the phenomenon that the output power of Nd:YAlO$_3$ crystal is limited due to the thermal effect of low-symmetry crystal, rather than Nd:YAlO$_3$ crystal's inherent deficiency. In 1979, the inventors theoretically illustrated the thermal effect of this crystal, thus founding scientific basis for correctly utilizing this crystal to design a high power laser (H. Y. Shen et al, "Influence of thermal effects on high power CW laser output of b-axis Nd:YAP", Chinese Physics, Vol. 3/1983, No. 1, p45). Presently, the inventors have developed a 1079.5 nm CW Nd:YAlO$_3$ laser with output power of 424 W (H. Y. Shen et al, "A high power 1079.5 nm Nd:YAlO$_3$ CW laser", Chinese Journal of Lasers, Vol. 19/1992, No. 1, p19). Moreover, the inventors established a new method to measure the laser stimulated emission cross section $\sigma$ and the fluorescent lifetime $\tau$. Table 1 lists the value of $\sigma\tau$ from $^4F_{3/2}-^4I_{13/2}$ transition of Nd$^{3+}$ ion doped YAlO$_3$ laser crystals with this measuring method. The corresponding values of other Nd$^{3+}$ doped laser crystals are also listed in this table as a comparison. Theoretically, the output power of CW laser is proportional to the value of $\sigma\tau$. From table 1, we know that the value $\sigma\tau$ in 1341.4 nm wavelength of Nd:YAlO$_3$ is larger than those of other Nd$^{3+}$ doped laser crystals. This measured result verifies the experiment result, namely that the output power of Nd:YAlO$_3$ crystal in $1.3\times10^3$ nm has an indisputable superiority. In addition, from Table 2, we know that the optical mechanical coefficient ($K_f$) of Nd:YAlO$_3$ crystal approaches that of Nd:YAG, so it has a good machining performance. Therefore, Nd:YAlO$_3$ crystal is a good laser crystal to develop 1341.4 nm high power CW lasers and large energy pulsed lasers. On the basis of this work, the inventors of this invention have developed a 1341.4 nm high power CW laser(H. Y. Shen et al, "Laser action of Nd:YAlO$_3$ at 1300 nm", Journal of Applied Physics, Vol. 70/1991, No. 6, p3373) and large energy pulsed laser (H. Y. Shen et al, "Large Energy 1341.4 nm Nd:YAlO$_3$ pulse laser", Opt. and Laser Technology, Vol. 23/1991, No. 6, p366) with output power of 195 W and output energy of 5 J, respectively. Consequently, the output power of that laser medical device using the Nd:YAlO$_3$ laser crystal is high enough to satisfy the power requirements (0–100 W) for clinical treatment.

TABLE 1

The parameters of some Nd$^{3+}$ doped laser crystals

| Crystal | Nd:YAG | Nd:YLF | Nd:BEL | Nd:YAlO$_3$ |
|---|---|---|---|---|
| $\tau(\mu s)$ $^4F_{3/2} - ^4I_{13/2}$ | 230 | 480 | 144 | 150 |
| $\lambda$(nm) | 1338/1318 | 1313 | 1351 | 1341.4 |
| $\sigma(\times 10^{-19}/cm^2)$ | 0.9/0.92 | 0.6 | 0.4 | 2.2 |
| $\sigma\tau(\times 10^{-19} \mu s/cm^2)$ | 207/211.6 | 288 | 57.6 | 330 |

TABLE 2

The values of $K_f$ of some laser materials

| Laser materials | Nd:YAG | Nd:YAlO$_3$ | Nd:Glass HoyaLHG8 | Nd:Glass ShottLG106 | Nd:Cr:GSGG |
|---|---|---|---|---|---|
| Value of $K_f$ ($\times 10^{-4}$ m$^{-1}$ KW$^{-1}$) | 3.8 | 4.29 | 7.8 | 17.0 | 22.5 |

Figure 2:
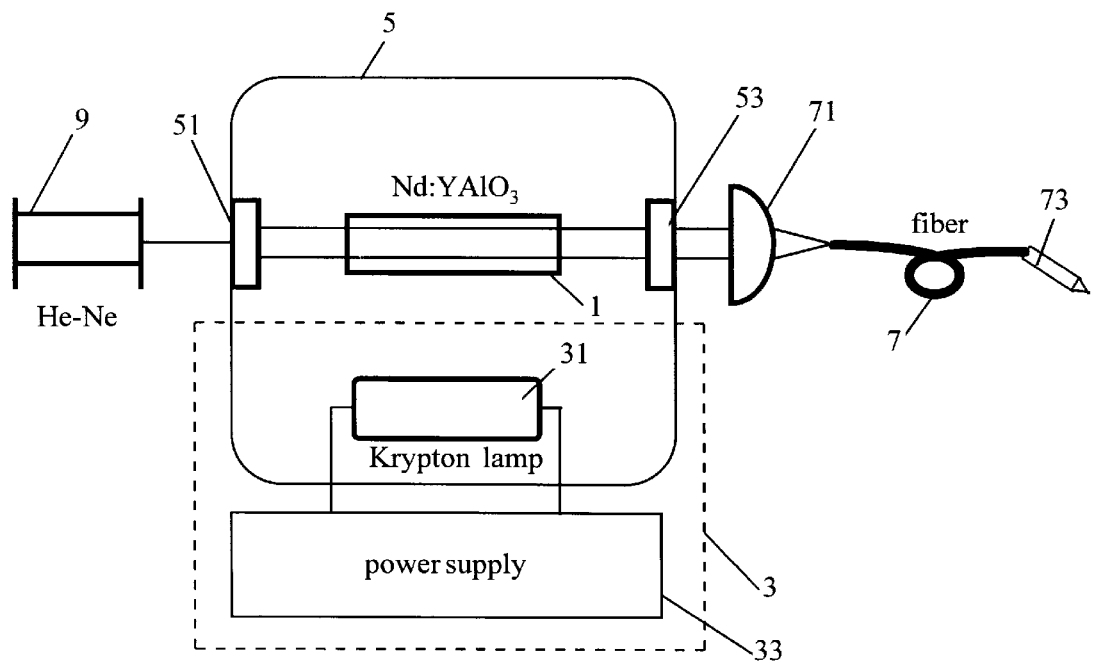
FIG. 2 is a diagram showing configuration of a CW laser medical device according to a preferred embodiment of the present invention.

FIG. 2 illustrates the constitution of the CW laser medical device of this invention. In FIG. 2, 1 designates Nd:YAlO$_3$ laser crystal, 3 designates the pumping system, 5 designates the laser cavity with a built-in laser crystal rod 1. Additionally, the pumping system 3 includes pumping light 31 (for example, it can be Krypton lamp), and the laser power supply which is used as the power source for pumping lamp 31. The laser cavity 5 includes reflector 51 and output mirror 53. Reflector 51 reflects almost all the laser light into the laser crystal 1, while output mirror 53 partially reflects the laser light, and from which part of the laser light outputs.

This CW laser medical device uses Nd:YAlO$_3$ laser crystal as its laser active medium, so the melted quartz is transparent for the laser light. For this reason, the output laser beam from the medical laser device can be transmitted by the general medical optical fibre. Thus, the device with such a function is convenient for a user to handle in therapy, especially in endoscopic operations. The medical laser device can also include: optical fibre 7 which is used to transmit laser light the convex lens which is located outside of output mirror 53 as an optical fibre injector 71, and which may also be integrated with output mirror 53, and through which the laser light is focused on an end of optical quartz fibre 7 with diameter 400–600 $\mu$m; and optical fibre pen 73 which is connected with another end of fibre 7 and through which the transmitted laser beam can be focused at the desired location with high power density.

The wavelengths of Nd:YAlO$_3$ laser drop in an invisible band, so the laser medical device can also include a red-light He—Ne laser 9 and its power supply (not shown). The beam of He—Ne laser 9 is, as shown in FIG. 2, aligned with the beam coming from Nd:YAlO$_3$ laser so as to guide Nd:YAlO$_3$ laser to aim at the needed location.

In order to make the laser work stably, it is ordinary to use a cooling system (not shown) to cool the laser crystal. The cooling system can be installed with other devices in one case, or be separately set as a twice cooling auto-circulating system. That system uses a well-known technology in the laser field, so its detailed structure is not illustrated here.

Figure 3:
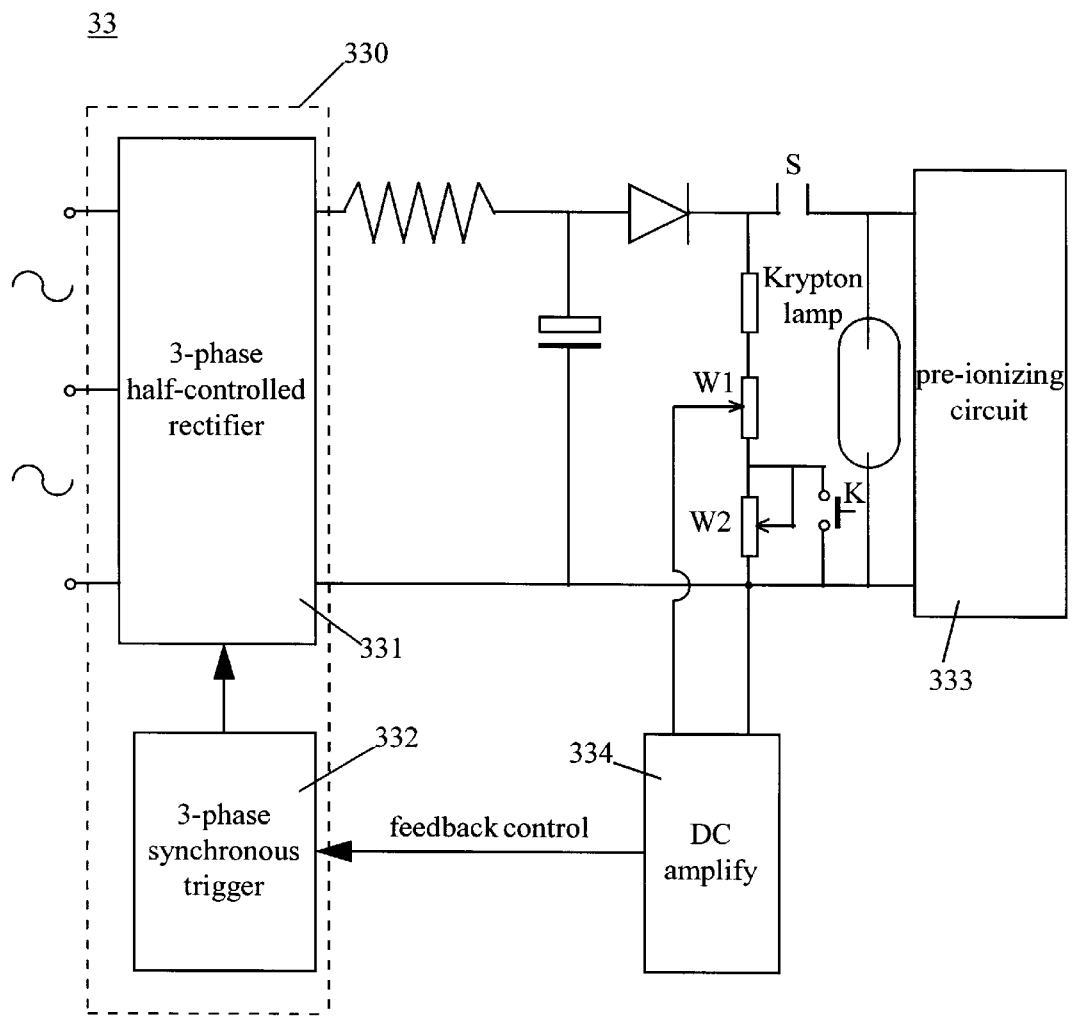
FIG. 3 is a schematic diagram of power supply for CW krypton pumping lamps used in the medical device shown in FIG. 2.

FIG. 3 illustrates the constitution of power supply 33 for the CW Krypton lamp shown in FIG. 2. In FIG. 3, 330 designates a direct current power supply which can convert 3-phase alternate current to direct current. This power supply is made of 3-phase half-controlled rectifier 331 and 3-phase synchronized phase-shifted trigger 332. Additionally, laser power supply 33 also includes pre-ionizing circuit 333 which can provide the Krypton lamp with the needed igniting current. S is a common open point of a controlling relay (not shown in FIG. 3). Before igniting Kr lamps, if the above-mentioned cooling system breaks down, or if the three-phase alternate current lacks any phase, S point will keep in open state; otherwise, S point will keep in close state. $W_1$ is a pre-set potential meter which can set the desired laser power in advance. $W_2$ is a controlling potential meter. Both $W_1$ and $W_2$ can adjust the laser power. K is a hand-switch or foot-handled switch to set $W_2$ short or open to control the output laser power. 334 is a direct current amplifier which takes the sample of output voltage of Kr lamps and feeds back to control the phase-shifted trigger in order to stabilize the output voltage in 0.5% fluctuation range.

Refer to FIG. 2 and FIG. 3 to see operation of the laser medical device. First, the cooling system is started, then the Kr lamps are switched on. If the cooling system or the three-phase current has any trouble, point S will be in open state, and a warning unit (not shown) will give an alarm; if both the cooling system and the three-phase current are normal, point S will become closed to connect laser power supply 33. Then, the He—Ne laser power supply is turned. The pre-set potential meter $W_1$ is adjusted to the laser power needed for the operation, and then the controlling potential meter $W_2$ is adjusted to set the laser power at zero (namely, lower than laser threshold). Then, using He—Ne laser as the aiming light at the focus of infection, the treadle switch K is turned on or hand-switch to short controlling potential meter $W_2$ so that the laser power immediately rises to the needed power for the operation. As soon as the operation is finished, the treadle-switch K is turned off and the laser power immediately return to zero. At the end, the controlling potential meter $W_2$ is adjusted to set the working current through the krypton lamp to 8–10 A, so that it will be convenient for doctors to operate, and prevent accidents caused by laser, and prolong lamp life, as well as economize on electricity.

As stated above, general quartz medical fibre is transparent at wavelength 1341.4 nm, and the laser power of $Nd:YAlO_3$ laser crystal has indisputable superiority. Thus, it is optimal to use $Nd:YAlO_3$ laser crystal in manufacturing 1341.4 nm $Nd:YAlO_3$ laser medical machines. Additionally, from the measured results of the absorption coefficients of distilled water and physiological saline at the wavelength of 1064 nm (Nd:YAG), 1079.5 nm ($Nd:YAlO_3$) and 1341.4 nm ($Nd:YAlO_3$), it shows that the absorption coefficient at 1341.4 nm is 12 times larger than that of laser at wavelength 1064 nm or 1079.5 nm. As we know, 70%–75% of a human body is composed of water, so 1341.4 nm laser light has a similar penetrating depth in skin as that of $CO_2$ 10.6 $\mu$m laser light and it is also a very effective tool to gasify or excise superficial disease tissue. Therefore, it is able to develop a kind of new and original 1341.4 nm laser medical device with optical fibre transmitting laser light, which has similar curative effects as those of the $CO_2$ laser medical device.

Figure 4:
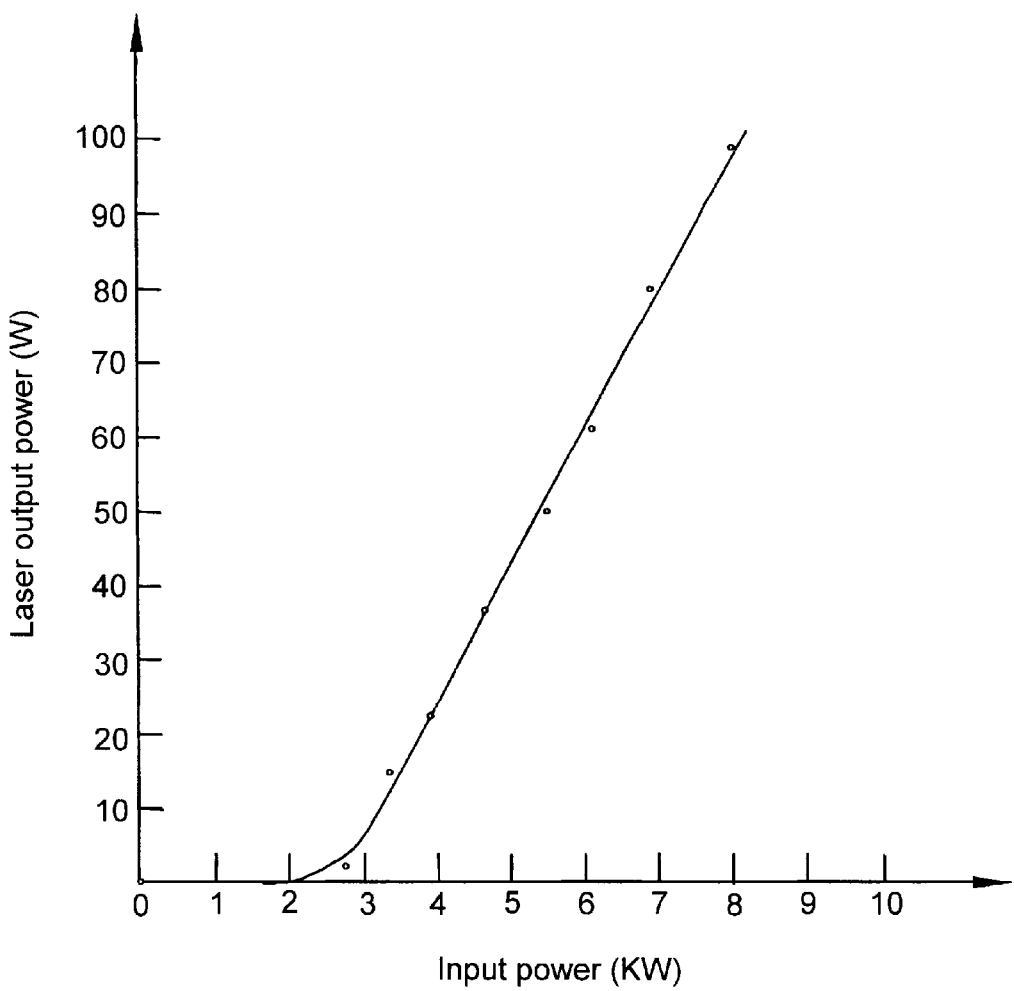
FIG. 4 is a curve of output power of a 1341.4 nm $Nd:YAlO_3$ CW laser medical device.

A 1341.4 nm $Nd:YAlO_3$ laser medical device can be a CW laser medical device as shown in FIG. 2, which uses CW Kr lamp as pumping light source. The laser crystal is an a-axis crystal rod at the size of 5–10 mm in diameter and 75–150 mm in length, and whose $Nd^{3+}$ doped density is 0.8–1.1 at %. Reflectivity at wavelength 1341.4 nm of the reflector of the resonator is 99.5%, and the coupler 97%–92%. When the input electricity power supply is adjusted from the range of 0–12 KW, 0–100 W 1341.4 nm laser light can be obtained from the output end of the optical fibre. The output curve of a 1341.4 nm $Nd:YAlO_3$ CW laser medical machine is shown in FIG. 4.

Figure 5:
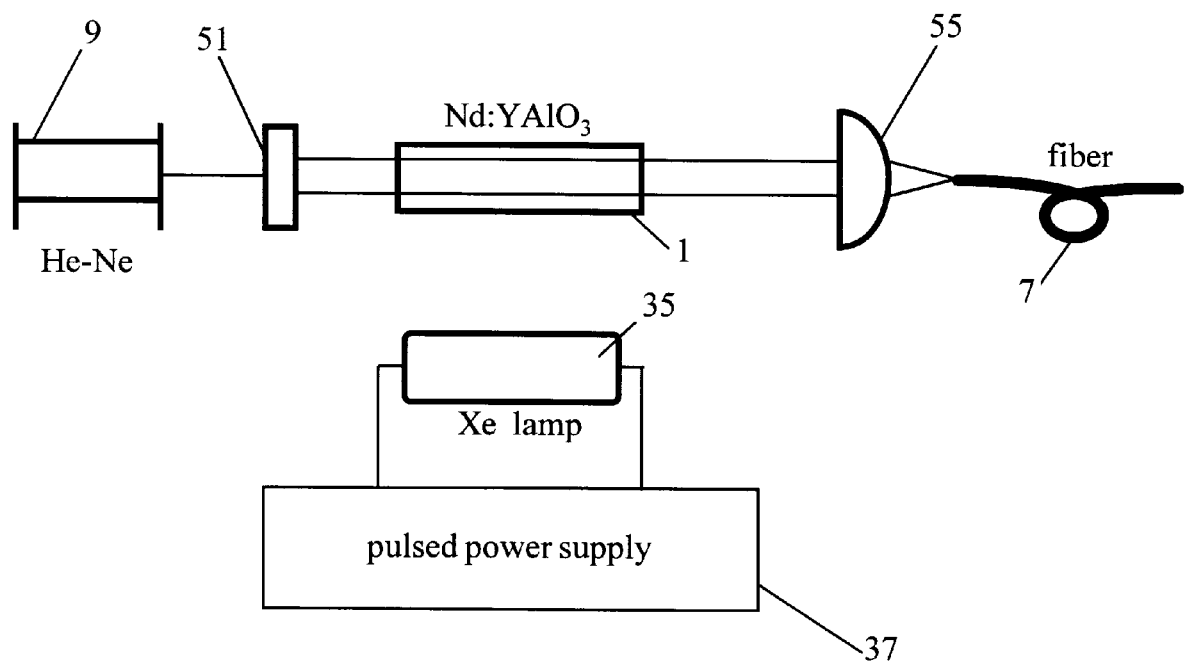
FIG. 5 is a diagram showing configuration of a pulsed laser medical device according to another preferred embodiment of the present invention.

A 1341.4 nm $Nd:YAlO_3$ laser medical machine can also be a pulsed laser medical device shown in FIG. 5, which uses pulse Xenon lamps as its pumping source. The laser crystal is an a-axis $Nd:YAlO_3$ crystal rod at the size of 5–6 mm in diameter and 75–110 mm in length, whose $Nd^{3+}$ doped density is 0.8–1.1 at %. Reflectivity for wavelength 1341.4 nm of the reflector of the resonator is 99.8%, and the coupler 60%–10%. When the input electricity energy supply 37 is adjusted from the range of 0–300 J, the corresponding output pulsed laser energy can be continuously adjusted from 0–5 J.

As mentioned above, 1341.4 nm $Nd:YAlO_3$ laser has had very good curative effects on superficial disease tissues, such as piles, freckles and angiomas.

Additionally, the absorption coefficient for 1079 nm is 12 times less than that for 1341.4 nm in distilled water and physiological saline, so the above-mentioned 1079.5 nm $Nd:YAlO_3$ laser has a large penetrating depth in skin. Thus, this kind of laser has good effects to solidify and stanch bleeding. Therefore, it is possible to provide a 1079.5 nm $Nd:YAlO_3$ laser medical device with optical fibre transmitting light having a good effect to stanch bleeding, by way of selecting appropriate parameters of a laser crystal as well as cavity and taking resonance conditions into account.

Moreover, as mentioned above, the output laser light from $Nd:YAlO_3$ is polarized, so resonator 5 can output polarized laser light. Even though the polarizability can decline when polarized light propagates through the optical fibre, the output light from the fibre still has partial polarizability. Compared with other unpolarized laser medical devices, such a polarized light has special effects on some diseases. For example, if using laser light to treat womb-neck erosion, $CO_2$ laser light cannot stop bleeding, Nd:YAG laser light will cause stomach upset, while $Nd:YAlO_3$ laser light can overcome these problems. If using laser light to treat a bone fracture, $Nd:YAlO_3$ laser light can promote a bone to grow faster, while other lasers such as $CO_2$ and Nd:YAG laser have no such therapeutic effect. Therefore, using an $Nd:YAlO_3$ crystal, $Nd:YAlO_3$ laser medical device outputting partially polarized light with special therapeutic effects can be produced.

Figure 6A:
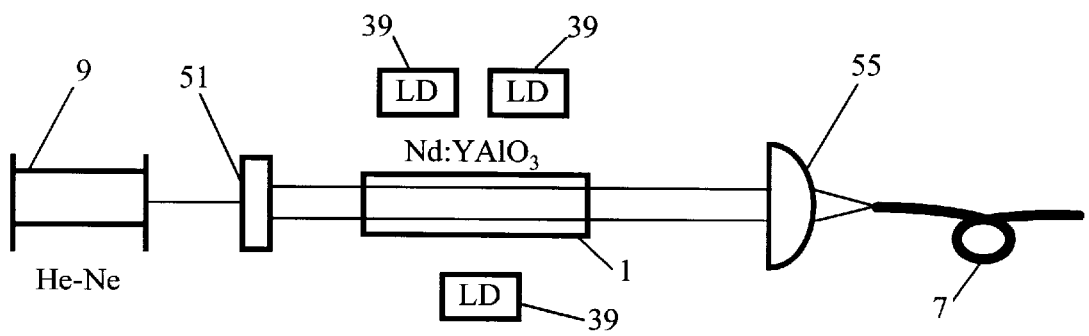
FIGS. 6(a) and 6(b) are schematic diagrams of laser diodes pumping laser medical devices.
Figure 6B:
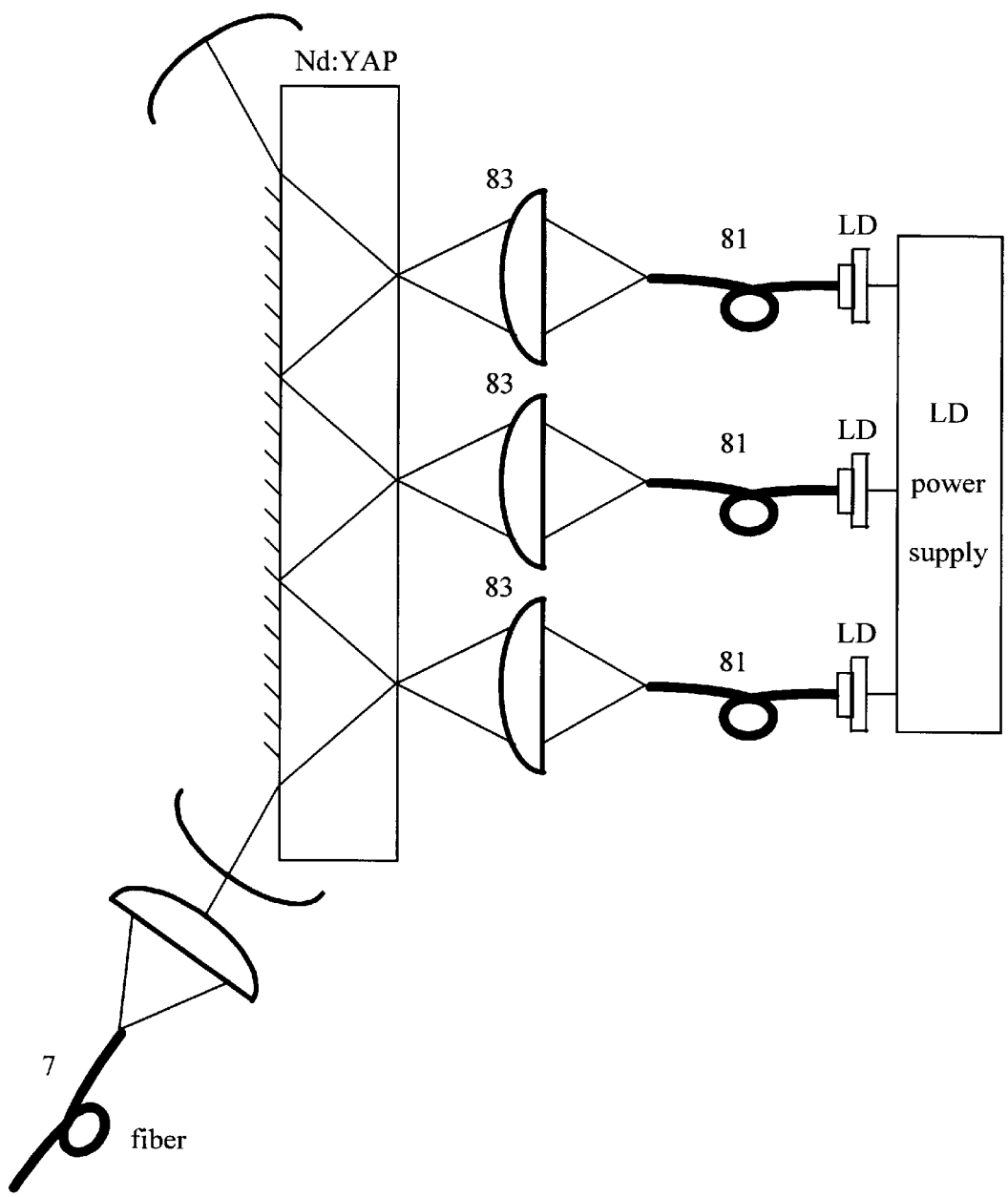

Presently the price of a laser diode is too expensive for being used as a pumping light source, but it should be understood that alongside the development of laser diode technology and the decrease of the prices, according to FIG. 6(*a*), one ordinary skilled in this art can use laser diode arrays 39 around laser crystal 1 as pumping light source and can also use optical fibre 81 according to FIG. 6(*b*) to transmit pumping light from laser diodes, and focus the light on laser crystal 1 by lens 83, thereby to manufacture a laser diode pumping $Nd:YAlO_3$ laser medical device.

It should be appreciated that all the modifications of the above-mentioned exemplary embodiments within the appended claims is not beyond the scope of this invention.

We claim:

1. A laser medical device comprising:

$Nd:YAlO_3$ laser crystal, a pumping system for illuminating said laser crystal with pumping light and achieving population inversion of $Nd^{3+}$ ion in said laser crystal, said pumping system including a pumping light source for irradiating said pumping light on said laser crystal, presetting means for setting in advance a value of output power of laser light adaptable to different medical treatment requirements, and a power supply for providing said pumping light source with a suitable input power based on said output power value set by said presetting means, and a resonant cavity for resonating light emitted from said $Nd^{3+}$ ion to produce a beam of output laser light having a predetermined wavelength at said output power, the wavelength of said laser light falling within a transparent range of quartz optical fibres so that said laser light is transmittable through said optical fibres to a therapy location of a subject.

2. The laser medical device as set forth in claim 1, wherein the wavelength of said laser light is 1341.4 nm.

3. The laser medical device as set forth in claim 1, wherein the wavelength of said laser light is 1079.5 nm.

4. The laser medical device as set forth in claim 1 wherein said laser light is of an intrinsic linear polarization.

5. The laser medical device as set forth in claim 1, wherein said pumping light source is a Krypton lamp.

6. The laser medical device as set forth in claim 1, wherein said pumping light source is a Xenon lamp.

7. The laser medical device as set forth in claim 1, wherein said power supply includes a CW power supply which is continuously adjustable so that said output power of said laser light is continuously variable from 0–100 watts.

8. The laser medical device as set forth in claim 1, wherein said power supply includes a pulsed energy supply which is continuously adjustable so that output energy of said laser light is continuously variable from 0–5 Joules.

9. The laser medical device as set forth in claim 1, wherein said pumping light source is a laser diode.

10. A laser medical device as set forth in claim 1, wherein said power supply includes a high repetition rate pulsed power supply which is continuously adjustable so that average output power of said laser light is variable from 0–100 watts.

11. A laser medical device adaptable to internal or external body treatments comprising:

Nd:YAlO$_3$ laser crystal, a pumping system for illuminating said laser crystal with pumping light and achieving population inversion of Nd$^{3+}$ ion in said laser crystals said pumping system including a pumping light source for irradiating said pumping light on said laser crystal, presetting means for setting in advance a value of output power of laser light adaptable to different medical treatment requirements, and a power supply for providing said pumping light source with a suitable input power based on said output power value set by said presetting means, a resonant cavity for resonating light emitted from said Nd$^{3+}$ ion to produce a beam of output laser light having a wavelength of 1341.4 nm at said output power, and an optical fibre for transmitting said 1341.4 nm laser light to a therapy location of a subject.

12. A laser medical device adaptable to internal or external body treatments comprising:

Nd:YAlO$_3$ laser crystal, a pumping system for illuminating said laser crystal with pumping light and achieving population inversion of Nd$^{3+}$ ion in said laser crystal, said pumping system including a pumping light source for irradiating said pumping light on said laser crystal, presetting means for setting in advance a value of output sower of laser light adaptable to different medical treatment requirements, and a power supply for providing said pumping light source with a suitable input power based on said output power value set by said presetting means, a resonant cavity for resonating light emitted from said Nd$^{3+}$ ion to produce a beam of output laser light having a wavelength of 1079.5 nm at said output power, and an optical fibre for transmitting said 1079.5 nm laser light to a therapy location of a subject.

13. A laser medical device adaptable to internal or external body treatments comprising:

Nd:YAlO$_3$ laser crystal;

a pumping system for illuminating said laser crystal with pumping light and achieving population inversion of Nd$^{3+}$ ion in said laser crystal, said pumping system including a pumping light source for irradiating said pumping light on said laser crystal, presetting means for setting in advance a value of output sower of laser light adaptable to different medical treatment requirements, and a power supply for providing said pumping light source with a suitable input power based on said output power value set by said presetting means, a resonant cavity for resonating light emitted from said Nd$^{3+}$ ion to produce a beam of output laser light having a predetermined wavelength with an intrinsic linear polarization at said output power, and an optical fibre for transmitting said linearly polarized laser light to a therapy location of a subject.

* * * * *